United States Patent
Amundson et al.

(10) Patent No.: US 12,131,475 B2
(45) Date of Patent: Oct. 29, 2024

(54) SYSTEMS AND METHODS FOR AUTOMATED DIGITAL IMAGE SELECTION AND PRE-PROCESSING FOR AUTOMATED CONTENT ANALYSIS

(71) Applicant: UnitedHealth Group Incorporated, Minnetonka, MN (US)

(72) Inventors: Russell H. Amundson, Merion Station, PA (US); Saurabh Bhargava, Eden Prairie, MN (US); Rama Krishna Singh, Greater Noida (IN); Ravi Pande, Noida (IN); Vishwakant Gupta, Noida (IN); Gaurav Mantri, Gurugram (IN); Abhinav Agrawal, Gulabpura (IN); Sapeksh Suman, Greater Noida West (IN)

(73) Assignee: UnitedHealth Group Incorporated, Minnetonka, MN (US)

( * ) Notice: Subject to any disclaimer, the term of this patent is extended or adjusted under 35 U.S.C. 154(b) by 821 days.

(21) Appl. No.: 17/191,868

(22) Filed: Mar. 4, 2021

(65) Prior Publication Data
US 2021/0295551 A1    Sep. 23, 2021

Related U.S. Application Data

(60) Provisional application No. 62/991,686, filed on Mar. 19, 2020.

(51) Int. Cl.
*G06T 7/00* (2017.01)
*G06F 18/2137* (2023.01)
(Continued)

(52) U.S. Cl.
CPC ...... *G06T 7/0014* (2013.01); *G06F 18/21375* (2023.01); *G06F 18/24* (2023.01);
(Continued)

(58) Field of Classification Search
CPC ... G06T 3/60; G06T 7/11; G06T 7/337; G06T 7/70; G06T 7/90; G06T 2207/10024; G06T 2207/20024
See application file for complete search history.

(56) References Cited

U.S. PATENT DOCUMENTS

| 4,688,780 A | 8/1987 | Hanz |
| 8,548,828 B1 | 10/2013 | Longmire |

(Continued)

OTHER PUBLICATIONS

NonFinal Office Action for U.S. Appl. No. 17/191,963, dated Aug. 18, 2023, (24 pages), United States Patent and Trademark Office, US.

(Continued)

*Primary Examiner* — Diane D Mizrahi
(74) *Attorney, Agent, or Firm* — Alston & Bird LLP

(57) ABSTRACT

Systems and methods are configured for preprocessing of images for further content based analysis thereof. Such images are extracted from a source data file, by standardizing individual pages within a source data file as image data files, and identifying whether the image satisfies applicable size-based criteria, applicable color-based criteria, and applicable content-based criteria, among others, utilizing one or more machine-learning based models. Various systems and methods may identify particular features within the extracted images to facilitate further image-based analysis based on the identified features.

21 Claims, 15 Drawing Sheets
(11 of 15 Drawing Sheet(s) Filed in Color)

(51) Int. Cl.

| | |
|---|---|
| *G06F 18/24* | (2023.01) |
| *G06T 3/60* | (2024.01) |
| *G06T 7/11* | (2017.01) |
| *G06T 7/33* | (2017.01) |
| *G06T 7/70* | (2017.01) |
| *G06T 7/90* | (2017.01) |
| *G06V 10/764* | (2022.01) |
| *G06V 10/77* | (2022.01) |
| *G16H 30/40* | (2018.01) |
| *G16H 40/67* | (2018.01) |

(52) U.S. Cl.
CPC .............. *G06T 3/60* (2013.01); *G06T 7/0012* (2013.01); *G06T 7/11* (2017.01); *G06T 7/337* (2017.01); *G06T 7/70* (2017.01); *G06T 7/90* (2017.01); *G06V 10/764* (2022.01); *G06V 10/7715* (2022.01); *G16H 30/40* (2018.01); *G16H 40/67* (2018.01); *G06T 2207/10024* (2013.01); *G06T 2207/20024* (2013.01); *G06T 2207/20081* (2013.01); *G06T 2207/20084* (2013.01); *G06T 2207/30004* (2013.01); *G06T 2207/30012* (2013.01); *G06T 2207/30068* (2013.01); *G06T 2207/30088* (2013.01); *G06T 2207/30096* (2013.01)

(56) References Cited

U.S. PATENT DOCUMENTS

| | | | |
|---|---|---|---|
| 8,898,798 | B2 | 11/2014 | Rogers et al. |
| 8,954,339 | B2 | 2/2015 | Schaffer |
| 10,242,443 | B2 | 3/2019 | Hsieh et al. |
| 2014/0064583 | A1 | 3/2014 | Wang et al. |
| 2014/0088989 | A1 | 3/2014 | Krishnapuram et al. |
| 2017/0330320 | A1 | 11/2017 | Lynch et al. |
| 2018/0040122 | A1 | 2/2018 | Kang et al. |
| 2018/0060512 | A1 | 3/2018 | Sorenson et al. |
| 2018/0342060 | A1 | 11/2018 | Yao et al. |
| 2019/0138693 | A1 | 5/2019 | Muller et al. |
| 2019/0392950 | A1 | 12/2019 | Conroy |
| 2020/0004561 | A1 | 1/2020 | Kottler et al. |
| 2020/0082507 | A1 | 3/2020 | Fang et al. |
| 2020/0085546 | A1 | 3/2020 | Li et al. |
| 2020/0258615 | A1 | 8/2020 | Goshen |
| 2021/0090694 | A1* | 3/2021 | Colley .................. G16H 15/00 |
| 2021/0174503 | A1 | 6/2021 | Trautwein |
| 2022/0019771 | A1 | 1/2022 | Matsunami |
| 2022/0039774 | A1 | 2/2022 | Wang et al. |

OTHER PUBLICATIONS

Notice of Allowance and Fees Due for U.S. Appl. No. 17/191,921, dated Aug. 22, 2023, (11 pages), United States Patent and Trademark Office, US.

"Eyelid Drooping—Blepharoptosis," RSIP Vision—Custom Medtech Imaging Algorithms, [article, online], (8 pages). [Retrieved from the Internet Jun. 7, 2021] <URL: https://www.rsipvision.com/eyelid-drooping-blepharoptosis/>.

"Pannus Is Not The Same Thing As Panniculus," Bariatric Pal, Apr. 22, 2014, (7 pages), [article, online]. [Retrieved from the Internet Jun. 7, 2021] <URL: https://www.bariatricpal.com/topic/305193-pannus-is-not-the-same-thing-as-panniculus/>.

"sovaSage—Reinventing Sleep Therapy," [online], (2 pages). [Retrieved from the Internet Jun. 7, 2021] <URL: https://www.sovasage.com/solution/>.

Borojeni, Azadeh A.T. et al. "Normative Ranges Of Nasal Airflow Variables In Healthy Adults," International Journal of Computer Assisted Radiology and Surgery, Jan. 2020, vol. 15, No. 1, pp. 87-98. doi: 10.1007/s11548-019-02023-y. Epub: Jul. 2, 2019, PMID: 31267334; PMCID: PMC6939154.

Cress, C. Ray. "Panniculus-Pannus," JAMA The Journal of the American Medical Association, vol. 226, No. 3, p. 353, Oct. 15, 1973. doi: 10.1001/jama.1973.03230030065024.

Froomkin, A. Michael et al. "When AIs Outperform Doctors: Confronting The Challenges Of A Tort-Induced Over-Reliance On Machine Learning," University of Miami School of Law Institutional Repository, vol. 61 Ariz. L. Rev. 33, Feb. 20, 2019, (68 pages).

Final Rejection Mailed on Feb. 16, 2024 for U.S. Appl. No. 17/191,963, 23 page(s).

Non-Final Rejection Mailed on Jun. 6, 2024 for U.S. Appl. No. 17/191,963, 16 page(s).

* cited by examiner

Back View

Front view – Shoulder visible
Front view – Shoulder Visible

SYSTEMS AND METHODS FOR AUTOMATED DIGITAL IMAGE SELECTION AND PRE-PROCESSING FOR AUTOMATED CONTENT ANALYSIS

CROSS-REFERENCE TO RELATED APPLICATIONS

This patent application claims priority to U.S. Provisional Appl. Ser. No. 62/991,686 filed Mar. 19, 2020, which is incorporated herein by reference in its entirety.

This patent application is additionally related to co-pending U.S. Patent Appl. Ser. No. 17/921,921, filed Mar. 4, 2021, and U.S. patent application Ser. No. 17/191,963, filed Mar. 4, 2021, both of which are incorporated herein by reference in their entirety.

BACKGROUND

Exchanging information relating to certain topics is facilitated by the inclusion of images as support for (or in place of) textual descriptions of information to be exchanged. These visual images may be particularly helpful in providing complete descriptions of certain medical conditions, through the use of photographs or other images generated through applicable imaging techniques (e.g., X-ray, Magnetic Resonance Imaging (MRI), CAT-scan, and/or the like). However, generated images have historically been unsuitable for automated review via computer-implemented systems, such as for automated diagnoses of medical conditions reflected within those images. Accordingly, a need exists for systems and methods configured for automated review of images to establish objective image content.

BRIEF SUMMARY

Various embodiments are directed to computing systems and methods configured for pre-processing images to enable detailed analysis of those images to determine image content. Certain embodiments are configured for selecting and extracting images from a variety of image sources and determining whether the included images are of sufficient resolution/size and/or quality to determine objective characteristics of the images. Moreover, the described systems and methods are configured for determining appropriate objective characteristics for evaluation within the images, for example, based at least in part on additional non-image data included within a data source. Based on determined objective characteristics for evaluation within the image data, the systems may be configured for determining whether the image content enables evaluation of the identified objective characteristics, for example, based on orientation of image content, identification of certain image components, and/or the like.

The pre-processing steps discussed in certain embodiments enables additional image analysis of image content, for example, utilizing objective criteria of image content so as to enable determinations of whether the image content satisfies defined rules, such as diagnosis-related rules for medical image analysis.

Certain embodiments are directed to a computer-implemented method for automated image extraction from a data source file, the method comprising: receiving a source data file containing one or more images; standardizing the source data file to a defined file type to generate a standardized source data file; performing histography color segmentation to identify images within the standardized source data file; extracting one or more identified images from the standardized source data file; executing a machine-learning based model for identifying features within extracted images; and aligning the extracted images based at least in part on the identified features.

In certain embodiments, the method further comprises executing a machine-learning based filtering model for filtering extracted images having a defined image type. In various embodiments, filtering extracted images having a defined image type comprises selecting full-color images. In certain embodiments, filtering extracted images having a defined image type comprises distinguishing between photographs and illustrations, and selecting the photographs. In certain embodiments, aligning the extracted images comprises rotating the extracted images based at least in part on the identified features. In various embodiments, the method further comprises receiving objective image analysis criteria; and executing a machine-learning based model to identify one or more finalized images of the one or more extracted images satisfying the objective image analysis criteria. In certain embodiments, the objective image analysis criteria defines an image content orientation.

Various embodiments are directed to an image analysis system configured for automated image extraction from a data source file, the image analysis system comprising: one or more non-transitory memory storage areas; and one or more processors collectively configured to: receive a source data file containing one or more images; standardize the source data file to a defined file type to generate a standardized source data file; perform histography color segmentation to identify images within the standardized source data file; extract one or more identified images from the standardized source data file; execute a machine-learning based model for identifying features within extracted images; and align the extracted images based at least in part on the identified features.

In certain embodiments, the one or more processors are further configured to: execute a machine-learning based filtering model for filtering extracted images having a defined image type. In various embodiments, filtering extracted images having a defined image type comprises selecting full-color images. In certain embodiments, filtering extracted images having a defined image type comprises distinguishing between photographs and illustrations, and selecting the photographs. Moreover, in certain embodiments, aligning the extracted images comprises rotating the extracted images based at least in part on the identified features. In certain embodiments, the one or more processors are further configured to: receive objective image analysis criteria; and execute a machine-learning based model to identify one or more finalized images of the one or more extracted images satisfying the objective image analysis criteria. In various embodiments, the objective image analysis criteria defines an image content orientation.

Certain embodiments are directed to a computer program product for identifying characteristics of features present within an image, the computer program product comprising at least one non-transitory computer-readable storage medium having computer-readable program code portions stored therein, the computer-readable program code portions configured to: receive a source data file containing one or more images; standardize the source data file to a defined file type to generate a standardized source data file; perform histography color segmentation to identify images within the standardized source data file; extract one or more identified images from the standardized source data file; execute a machine-learning based model for identifying features within extracted images; and align the extracted images based at least in part on the identified features.

In certain embodiments, the computer program product further comprises one or more executable portions configured to: execute a machine-learning based filtering model for filtering extracted images having a defined image type. In certain embodiments, filtering extracted images having a defined image type comprises selecting full-color images. In certain embodiments, filtering extracted images having a defined image type comprises distinguishing between photographs and illustrations, and selecting the photographs. In various embodiments, aligning the extracted images comprises rotating the extracted images based at least in part on the identified features. In various embodiments, the computer program product further comprises one or more executable portions configured to: receiving objective image analysis criteria; and executing a machine-learning based model to identify one or more finalized images of the one or more extracted images satisfying the objective image analysis criteria. In certain embodiments, the objective image analysis criteria defines an image content orientation.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Reference will now be made to the accompanying drawings, which are not necessarily drawn to scale, and wherein.

DETAILED DESCRIPTION

Figure 1:
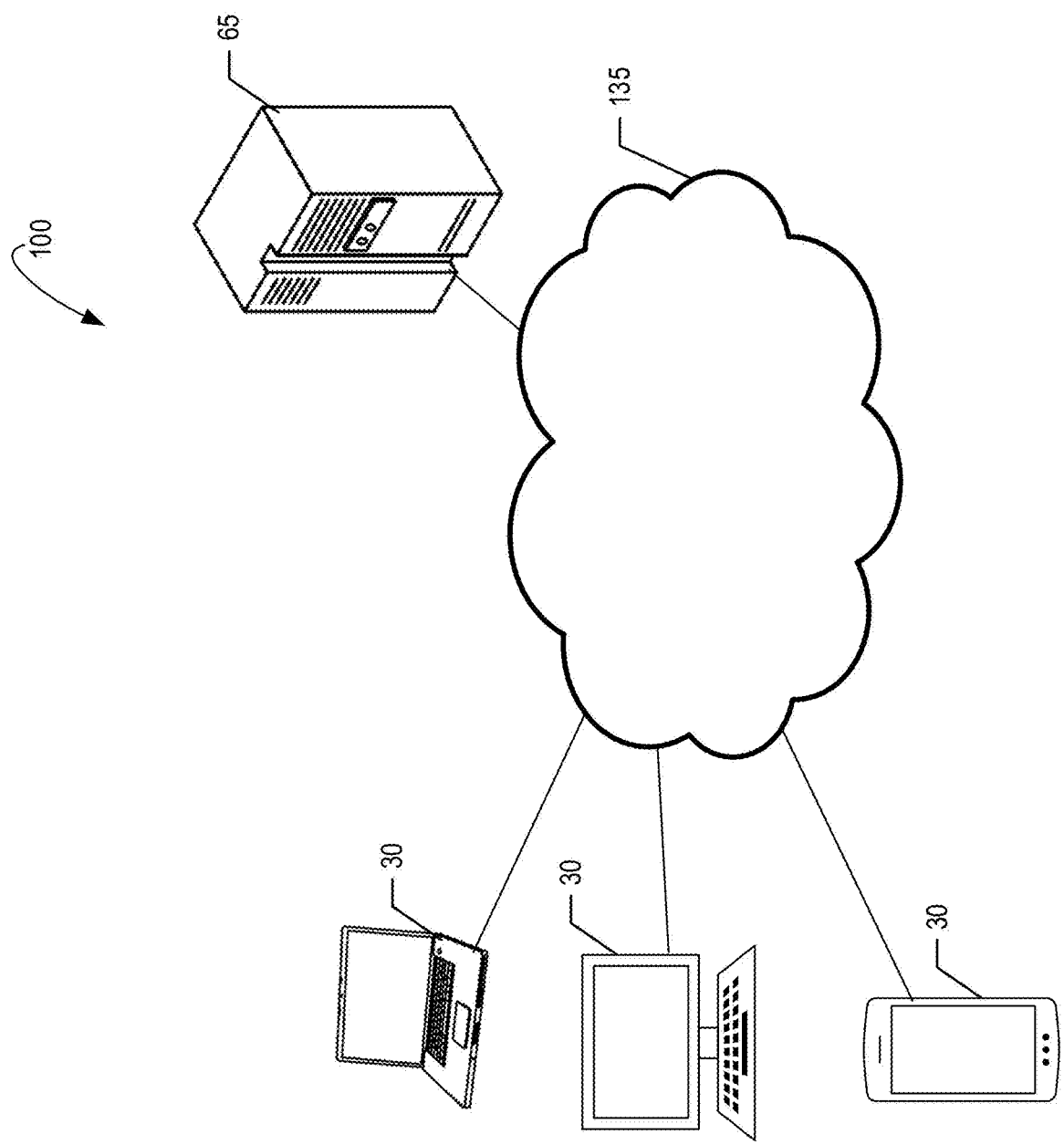
FIG. 1 is a diagram of a system that can be used in conjunction with various embodiments of the present invention.

The present disclosure more fully describes various embodiments with reference to the accompanying drawings. It should be understood that some, but not all embodiments are shown and described herein. Indeed, the embodiments may take many different forms, and accordingly this disclosure should not be construed as limited to the embodiments set forth herein. Rather, these embodiments are provided so that this disclosure will satisfy applicable legal requirements. Like numbers refer to like elements throughout.

I. COMPUTER PROGRAM PRODUCTS, METHODS, AND COMPUTING ENTITIES

Embodiments of the present invention may be implemented in various ways, including as computer program products that comprise articles of manufacture. Such computer program products may include one or more software components including, for example, software objects, methods, data structures, and/or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magneto resistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of a data structure, apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

II. EXEMPLARY SYSTEM ARCHITECTURE

FIG. 1 provides an illustration of a system 100 that can be used in conjunction with various embodiments of the present invention. As shown in FIG. 1, the system 100 may comprise one or more image analysis systems 65, one or more user computing entities 30 (e.g., which may encompass handheld computing devices, laptop computing devices, desktop computing devices, and/or one or more Internet of Things (IoT) devices, and/or the like, one or more networks 135, and/or the like. Each of the components of the system may be in electronic communication with, for example, one another over the same or different wireless or wired networks 135 including, for example, a wired or wireless Personal Area Network (PAN), Local Area Network (LAN), Metropolitan Area Network (MAN), Wide Area Network (WAN), and/or the like. Additionally, while FIG. 1 illustrate certain system entities as separate, standalone entities, the various embodiments are not limited to this particular architecture.

a. Exemplary Image Analysis System

Figure 2:
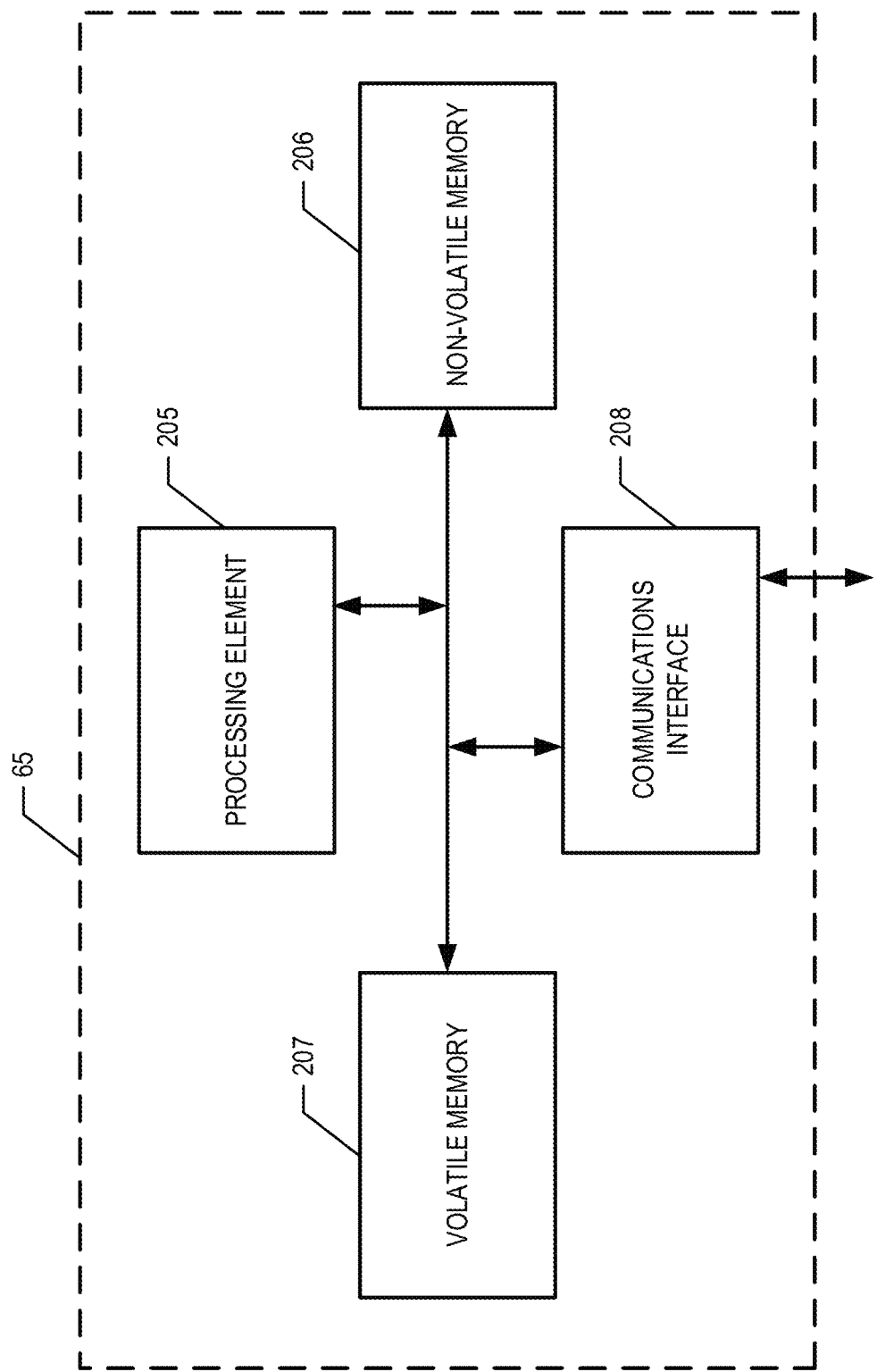
FIG. 2 is a schematic of an image analysis system in accordance with certain embodiments of the present invention.

FIG. 2 provides a schematic of an image analysis system 65 according to one embodiment of the present invention. In general, the terms computing entity, entity, device, system, and/or similar words used herein interchangeably may refer to, for example, one or more computers, computing entities, desktop computers, mobile phones, tablets, phablets, notebooks, laptops, distributed systems, items/devices, terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the image analysis system 65 may also include one or more network and/or communications interfaces 208 for communicating with various computing entities, such as by communicating data, content, information, and/or similar terms used herein interchangeably that can be transmitted, received, operated on, processed, displayed, stored, and/or the like. For instance, the image analysis system 65 may communicate with other computing entities, one or more user computing entities 30, and/or the like.

As shown in FIG. 2, in one embodiment, the image analysis system 65 may include or be in communication with one or more processing elements 205 (also referred to as processors, processing circuitry, and/or similar terms used herein interchangeably) that communicate with other elements within the image analysis system 65 via a bus, for example, or network connection. As will be understood, the processing element 205 may be embodied in a number of different ways. For example, the processing element 205 may be embodied as one or more complex programmable logic devices (CPLDs), microprocessors, multi-core processors, coprocessing entities, application-specific instruction-set processors (ASIPs), and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the image analysis system 65 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 206 as described above, such as hard disks, ROM, PROM, EPROM, EEPROM, flash memory, MMCs, SD memory cards, Memory Sticks, CBRAM, PRAM, FeRAM, RRAM, SONOS, racetrack memory, and/or the like. As will be recognized, the non-volatile storage or memory media may store databases, metadata repositories database instances, database management system entities, data, applications, programs, program modules, scripts, source code, object code, byte code, compiled code, interpreted code, machine code, executable instructions, and/or the like. The term database, database instance, database management system entity, and/or similar terms used herein interchangeably and in a general sense to refer to a structured or unstructured collection of information/data that is stored in a computer-readable storage medium.

Memory media 206 (e.g., metadata repository) may also be embodied as a data storage device or devices, as a separate database server or servers, or as a combination of data storage devices and separate database servers. Further, in some embodiments, memory media 206 may be embodied as a distributed repository such that some of the stored information/data is stored centrally in a location within the system and other information/data is stored in one or more remote locations. Alternatively, in some embodiments, the distributed repository may be distributed over a plurality of remote storage locations only. An example of the embodiments contemplated herein would include a cloud data storage system maintained by a third-party provider and where some or all of the information/data required for the operation of the system may be stored. As a person of ordinary skill in the art would recognize, the information/data required for the operation of the system may also be partially stored in the cloud data storage system and partially stored in a locally maintained data storage system.

Memory media 206 (e.g., metadata repository) may include information/data accessed and stored by the system to facilitate the operations of the system. More specifically, memory media 206 may encompass one or more data stores configured to store information/data usable in certain embodiments. Data stored within such data repositories may be utilized during operation of various embodiments as discussed herein.

In one embodiment, the image analysis system 65 may further include or be in communication with volatile media (also referred to as volatile storage, memory, memory storage, memory circuitry and/or similar terms used herein interchangeably). In one embodiment, the volatile storage or memory may also include one or more volatile storage or memory media 207 as described above, such as RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. As will be recognized, the volatile storage or memory media may be used to store at least portions of the databases, database instances, database management system entities, data, applications, programs, program modules, scripts, source code, object code, byte code, compiled code, interpreted code, machine code, executable instructions, and/or the like being executed by, for example, the processing element 205. Thus, the databases, database instances, database management system entities, data, applications, programs, program modules, scripts, source code, object code, byte code, compiled code, interpreted code, machine code, executable instructions, and/or the like may be used to control certain aspects of the operation of the image analysis system 65 with the assistance of the processing element 205 and operating system.

As indicated, in one embodiment, the image analysis system 65 may also include one or more network and/or communications interfaces 208 for communicating with various computing entities (e.g., user computing entities 30), such as by communicating data, content, information, and/or similar terms used herein interchangeably that can be transmitted, received, operated on, processed, displayed, stored, and/or the like. For instance, the image analysis system 65 may communicate with computing entities or communication interfaces of other computing entities, user computing entities 30, and/or the like. In this regard, the image analysis system 65 may access various data assets.

As indicated, in one embodiment, the image analysis system 65 may also include one or more network and/or communications interfaces 208 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the image analysis system 65 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol. The image analysis system 65 may use such protocols and standards to communicate using Border Gateway Protocol (BGP), Dynamic Host Configuration Protocol (DHCP), Domain Name System (DNS), File Transfer Protocol (FTP), Hypertext Transfer Protocol (HTTP), HTTP over TLS/SSL/Secure, Internet Message Access Protocol (IMAP), Network Time Protocol (NTP), Simple Mail Transfer Protocol (SMTP), Telnet, Transport Layer Security (TLS), Secure Sockets Layer (SSL), Internet Protocol (IP), Transmission Control Protocol (TCP), User Datagram Protocol (UDP), Datagram Congestion Control Protocol (DCCP), Stream Control Transmission Protocol (SCTP), Hypertext Markup Language (HTML), and/or the like.

As will be appreciated, one or more of the image analysis system's components may be located remotely from other image analysis system 65 components, such as in a distributed system. Furthermore, one or more of the components may be aggregated and additional components performing functions described herein may be included in the image analysis system 65. Thus, the image analysis system 65 can be adapted to accommodate a variety of needs and circumstances.

b. Exemplary User Computing Entity

Figure 3:
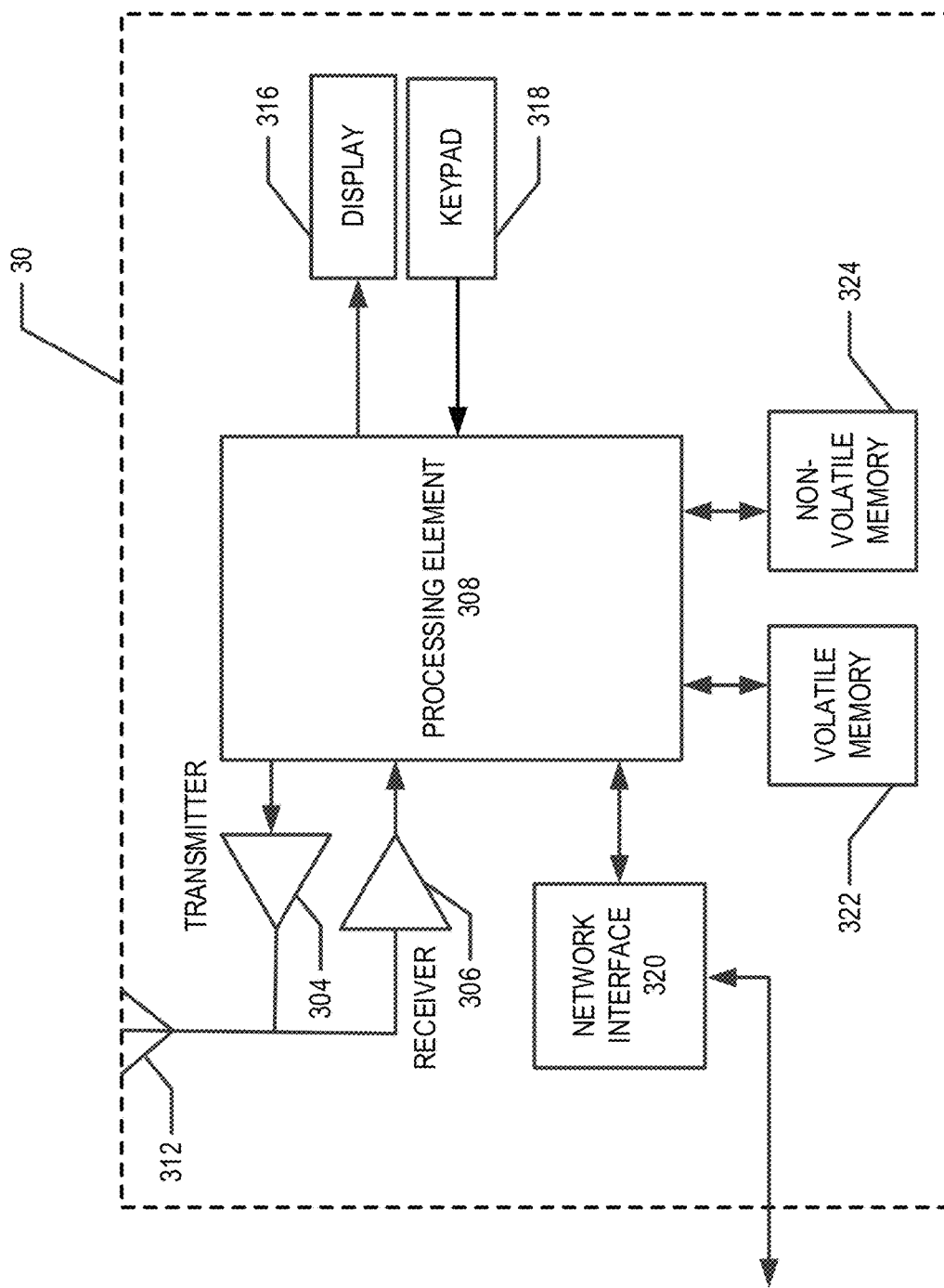
FIG. 3 is a schematic of a user computing entity in accordance with certain embodiments of the present invention.

FIG. 3 provides an illustrative schematic representative of user computing entity 30 that can be used in conjunction with embodiments of the present invention. As will be recognized, the user computing entity 30 may be operated by an agent and include components and features similar to those described in conjunction with the image analysis system 65. Further, as shown in FIG. 3, the user computing entity 30 may include additional components and features. For example, the user computing entity 30 can include an antenna 312, a transmitter 304 (e.g., radio), a receiver 306 (e.g., radio), and a processing element 308 that provides signals to and receives signals from the transmitter 304 and receiver 306, respectively. The signals provided to and received from the transmitter 304 and the receiver 306, respectively, may include signaling information/data in accordance with an air interface standard of applicable wireless systems to communicate with various entities, such as an image analysis system 65, another user computing entity 30, and/or the like. In this regard, the user computing entity 30 may be capable of operating with one or more air interface standards, communication protocols, modulation types, and access types. More particularly, the user computing entity 30 may operate in accordance with any of a number of wireless communication standards and protocols. In a particular embodiment, the user computing entity 30 may operate in accordance with multiple wireless communication standards and protocols, such as GPRS, UMTS, CDMA2000, 1×RTT, WCDMA, TD-SCDMA, LTE, E-UTRAN, EVDO, HSPA, HSDPA, Wi-Fi, WiMAX, UWB, IR protocols, Bluetooth protocols, USB protocols, and/or any other wireless protocol.

Via these communication standards and protocols, the user computing entity 30 can communicate with various other entities using concepts such as Unstructured Supplementary Service data (USSD), Short Message Service (SMS), Multimedia Messaging Service (MMS), Dual-Tone Multi-Frequency Signaling (DTMF), and/or Subscriber Identity Module Dialer (SIM dialer). The user computing entity 30 can also download changes, add-ons, and updates, for instance, to its firmware, software (e.g., including executable instructions, applications, program modules), and operating system.

According to one embodiment, the user computing entity 30 may include location determining aspects, devices, modules, functionalities, and/or similar words used herein interchangeably. For example, the user computing entity 30 may include outdoor positioning aspects, such as a location module adapted to acquire, for example, latitude, longitude, altitude, geocode, course, direction, heading, speed, UTC, date, and/or various other information/data. In one embodiment, the location module can acquire data, sometimes known as ephemeris data, by identifying the number of satellites in view and the relative positions of those satellites. The satellites may be a variety of different satellites, including LEO satellite systems, DOD satellite systems, the European Union Galileo positioning systems, the Chinese Compass navigation systems, Indian Regional Navigational satellite systems, and/or the like. Alternatively, the location information/data/data may be determined by triangulating the position in connection with a variety of other systems, including cellular towers, Wi-Fi access points, and/or the like. Similarly, the user computing entity 30 may include indoor positioning aspects, such as a location module adapted to acquire, for example, latitude, longitude, altitude, geocode, course, direction, heading, speed, time, date, and/or various other information/data. Some of the indoor aspects may use various position or location technologies including RFID tags, indoor beacons or transmitters, Wi-Fi access points, cellular towers, nearby computing devices (e.g., smartphones, laptops) and/or the like. For instance, such technologies may include iBeacons, Gimbal proximity beacons, BLE transmitters, Near Field Communication (NFC) transmitters, and/or the like. These indoor positioning aspects can be used in a variety of settings to determine the location of someone or something to within inches or centimeters.

The user computing entity 30 may also comprise one or more user input/output interfaces (e.g., a display 316 and/or speaker/speaker driver coupled to a processing element 308 and a touch screen, keyboard, mouse, and/or microphone coupled to a processing element 308). For example, the user output interface may be configured to provide an application, browser, user interface, dashboard, webpage, and/or similar words used herein interchangeably executing on and/or accessible via the user computing entity 30 to cause display or audible presentation of information/data and for user interaction therewith via one or more user input interfaces. The user output interface may be updated dynamically from communication with the image analysis system 65. The user input interface can comprise any of a number of devices allowing the user computing entity 30 to receive information/data, such as a keypad 318 (hard or soft), a touch display, voice/speech or motion interfaces, scanners, readers, or other input device. In embodiments including a keypad 318, the keypad 318 can include (or cause display of) the conventional numeric (0-9) and related keys (#, *), and other keys used for operating the user computing entity 30 and may include a full set of alphabetic keys or set of keys that may be activated to provide a full set of alphanumeric keys. In addition to providing input, the user input interface can be used, for example, to activate or deactivate certain functions, such as screen savers and/or sleep modes. Through such inputs the user computing entity 30 can collect information/data, user interaction/input, and/or the like.

The user computing entity 30 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, RRAM, SONOS, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. The volatile and non-volatile storage or memory can store databases, database instances, database management system entities, data, applications, programs, program modules, scripts, source code, object code, byte code, compiled code, interpreted code, machine code, executable instructions, and/or the like to implement the functions of the user computing entity 30.

c. Exemplary Networks

In one embodiment, the networks 135 may include, but are not limited to, any one or a combination of different types of suitable communications networks such as, for example, cable networks, public networks (e.g., the Internet), private networks (e.g., frame-relay networks), wireless networks, cellular networks, telephone networks (e.g., a public switched telephone network), or any other suitable private and/or public networks. Further, the networks 135 may have any suitable communication range associated therewith and may include, for example, global networks (e.g., the Internet), MANs, WANs, LANs, or PANs. In addition, the networks 135 may include any type of medium over which network traffic may be carried including, but not limited to, coaxial cable, twisted-pair wire, optical fiber, a hybrid fiber coaxial (HFC) medium, microwave terrestrial transceivers, radio frequency communication mediums, satellite communication mediums, or any combination thereof, as well as a variety of network devices and computing platforms provided by network providers or other entities.

II. EXEMPLARY SYSTEM OPERATION

Details regarding various embodiments are described with respect to FIGS. 4-9B herein, which illustrate various images analyzed and/or otherwise generated by an image analysis system as discussed herein.

a. Overview

Certain embodiments are configured for automated image extraction and pre-processing to enable automated computer-based analysis of image contents. Computer-implemented methods and corresponding systems are configured for executing image analysis models to extract images from an image data source that may comprise multiple information mediums (e.g., text and images) to enable execution of image-specific data analyses. Moreover, to ensure that the extracted images constitute a specified image type that is appropriate for further analysis, and for ensuring that the extracted images are of a sufficient image quality to enable detailed image analysis, the described systems and methods are configured for implementing various image-based analytical models, including certain machine-learning based models for pre-processing and/or selecting images for further analysis. Such pre-processing steps may be based at least in part on a type of content-based analysis to be performed for the image, and accordingly the described systems and methods may retrieve one or more analysis-specific image criteria defining expected contents of an image for further analysis (as well as characteristics of those expected contents) so as to enable selection of a subset of extracted images to be representative images of the contents of the original data file for further analysis.

1. Technical Problem

Image analysis has historically required at least some amount of manual review to make objective and subjective determinations regarding the contents of those images. Particularly when reviewing images of multiple subjects having distinguishing features (e.g., photographing humans), structured rule-based analyses of those images may be difficult to automate in light of the distinguishing features present within each image. Moreover, the subject matter of individual images may have different perspectives, (e.g., slight variations in orientation of an imaging device versus the subject matter of the image), which may impact the ability to perform objective comparisons between the subject matter of an individual image and corresponding analytical requirements. Such inherent differences in image data contents impede the use of automated systems and methods for analyzing contents of images.

2. Technical Solution

To address the inherently technical challenges associated with analyzing the content of individual images and/or other files containing one or more images, various embodiments utilize a structured series of analytical modules each performing image extraction, image filtering, image editing, and/or image review processes to ensure images are of sufficient quality to enable application of detailed content-based objective analysis of the image data. Certain embodiments utilize image-specific data analyses to extract images of a sufficient size and/or quality, and then apply one or more machine-learning based models to determine whether the contents of the image satisfy defined characteristics suitable for performing objective analysis of the contents of the image.

b. Image Extraction

Image analysis systems 65 in accordance with certain embodiments operate together with an intake mechanism configured to intake source data files. These source data files may be received from any of a variety of data sources, such as directly from individual user computing entities 30, from external systems (e.g., electronic health record systems operating to store medical notes received from individual care providers relating to individual patients, and/or the like). Moreover, when embodiments as discussed herein are implemented in a medical record context, the image analysis system 65 may be implemented as a part of a medical record storage system satisfying applicable privacy requirements for maintaining adequate patient privacy. In certain embodiments, the image analysis system 65 may be configured to only temporarily store any analyzed images before providing those images to applicable downstream analysis systems and subsequently erasing any temporarily stored images. In other embodiments the output may constitute text-based analysis that does not itself contain any patient-identifiable data, and such data may be added to existing patient data records, while any images generated may be deleted. In yet other embodiments, the results of any image analysis may be stored as images within a corresponding patient record while maintaining adequate patient privacy.

Figure 4:
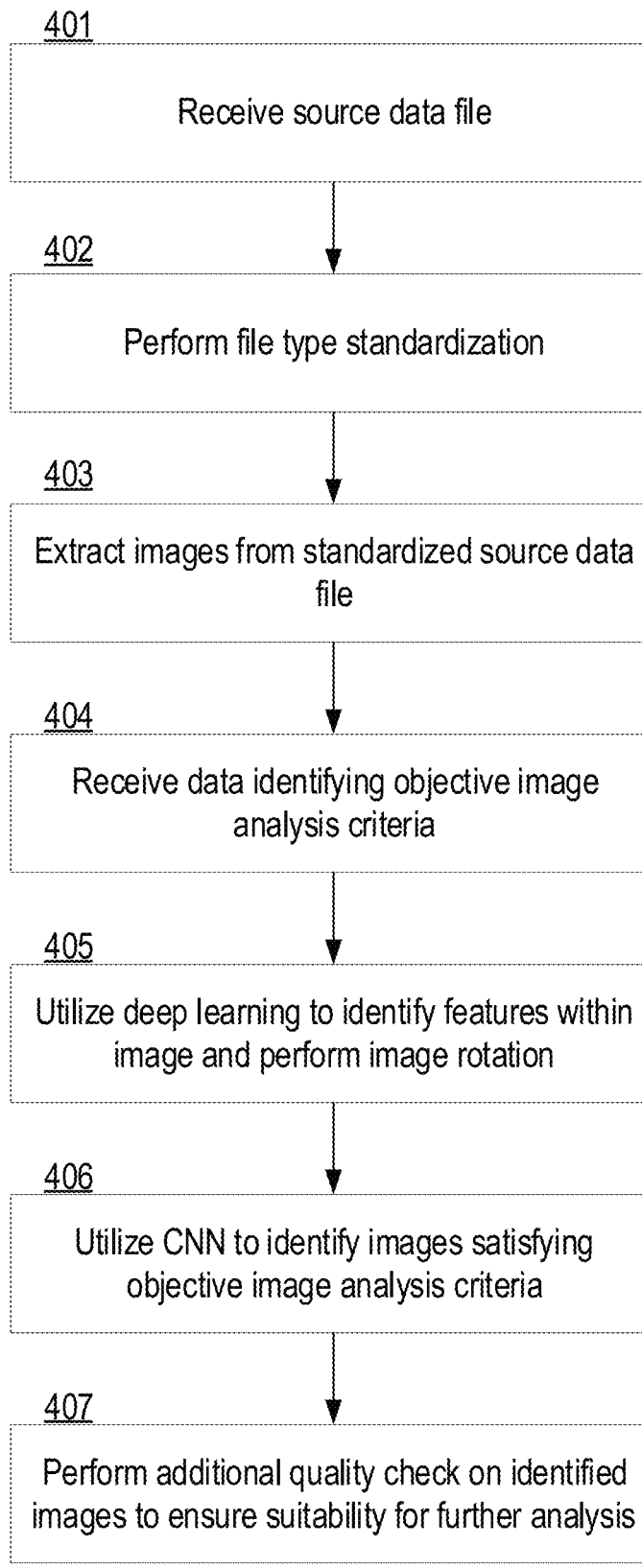
FIG. 4 is a flow diagram illustrating operation of processing images according to certain embodiments.

FIG. 4 illustrates a flowchart of example processes associated with preparing images for further automated analysis in accordance with applicable image analysis. As shown at Block 401, the image analysis system 65 is configured to receive a source data file comprising one or more images. The image analysis system 65 may utilize any of a variety of mechanisms for intaking data files, such as application program interfaces (APIs) configured to identify a particular source data file, a file intake channel such as a File Transfer Protocol (FTP) system, a Cross File Transfer (CFT) system, SSH File Transfer Protocol (SFTP), an Enterprise Clinical Archive System (ECAS), a file upload system, an email system, via accessing file repositories (e.g., third party file repositories), a website in communication with the image analysis system, a locally stored application of a user computing entity managed by the image analysis system 65, and/or the like. Moreover, the image analysis system 65 may be configured for receiving source data files of a plurality of data file types, such as PDFs, image files (e.g., .jpg, .gif, tiff, and/or the like), document files, spreadsheet files, webpage files, and/or the like.

In order to enable processing of any of the plurality of file types, the image analysis system 65 is configured to convert the received source data files into a standardized file type as indicated at Block 402. Source file standardization may comprises receiving a plurality of data files relating to a particular patient, a particular case, a particular medical visit, and/or the like. As noted above, these multiple files may comprise any of a variety of file types, such as PDFs, image files, and/or the like. The image analysis system 65 receives these plurality of data files and stores these data files within a unique directory generated within a storage repository for further processing. The image analysis system 65 then converts each page within each data file into an image file (e.g., by converting each PDF page into a jpg or other standardized image file type). The generated image files are stored within the unique directory noted above. Other images may be converted to the same image type, thereby standardizing the images for further analysis. Further processing as discussed herein may be performed individually on each generated image data file stored within the unique directory.

c. Image Sizing

Once all relevant documents have been ingested and stored within a relevant data repository (and each document is standardized into an image data file type), the image analysis system 65 identifies embedded images within those stored data files that are of sufficient size and quality to support further content-based analysis of the embedded images. These images may be photographs, scan-generated images (e.g., X-ray, MRI, CAT-scan, and/or the like), or other images deemed relevant for content-based analysis.

Particularly when analyzing embedded images within explanatory documentation (e.g., images embedded within a PDF document having a plurality of text-based portions) the embedded images may constitute a small portion of the overall explanation, and those embedded images may be present only within a subset of pages of the original document. Accordingly, to identify relevant embedded images within the plurality of standardized image data files, the image analysis system 65 extracts embedded images as indicated at Block 403, for example, by performing a histogram color segmentation analysis to determine the overall ratio of white versus non-white pixels (or white versus black pixels) within an image data file to identify those image data files (e.g., generated from individual pages within an originally submitted documentation) comprising embedded images of sufficient size to enable further analysis.

The histogram color segmentation analysis analyzes each pixel within an image data file to determine color values associated therewith. These color values may be RGB color values or other color values that may be indicative of a shade or color of the pixel. Each pixel may then be classified as white (e.g., having a value of 255 for each of Red, Green, and Blue color channels), black (e.g., having a value of 0 for each of Red, Green, and Blue color channels), or other (e.g., pixels that are neither white nor black). The image analysis system 65 may utilize thresholds to differentiate between white, black, and other colors (e.g., those pixels having color values above a white threshold may be considered white; those pixels having color values below a black threshold may be considered black; and/or the like). However, it should be understood that other values for distinguishing between white, black, and other pixels may be utilized. Upon identifying color values for each pixel, the image analysis system 65 may be configured to generate a color profile for the image data file, indicating an overall percentage of white pixels, black pixels, and/or other pixels within the image data file. The image analysis system 65 may then compare the color profile for the image data file against one or more thresholds to identify those image data files comprising embedded images of suitable size for further analysis. For example, the image data analysis 65 may determine whether the image profile for an image data file indicates that the image data file comprises a percentage of black pixels greater than a threshold percentage (e.g., 75%) and/or a percentage of white pixels greater than a threshold percentage (e.g., 75%) to determine whether the image data file contains embedded images of suitable quality for further analysis. Further to the above example, if the image data file comprises more black pixels than the threshold amount or if the image data file comprises more white pixels than the threshold amount, the image data file may be determined to be unsuitable for further analysis. The image analysis system 65 may then flag those image data files as irrelevant for further analysis (e.g., by updating metadata associated with those image data files with a relevant flag; by discarding those image data files from the data storage directory; and/or the like).

Figure 5B:
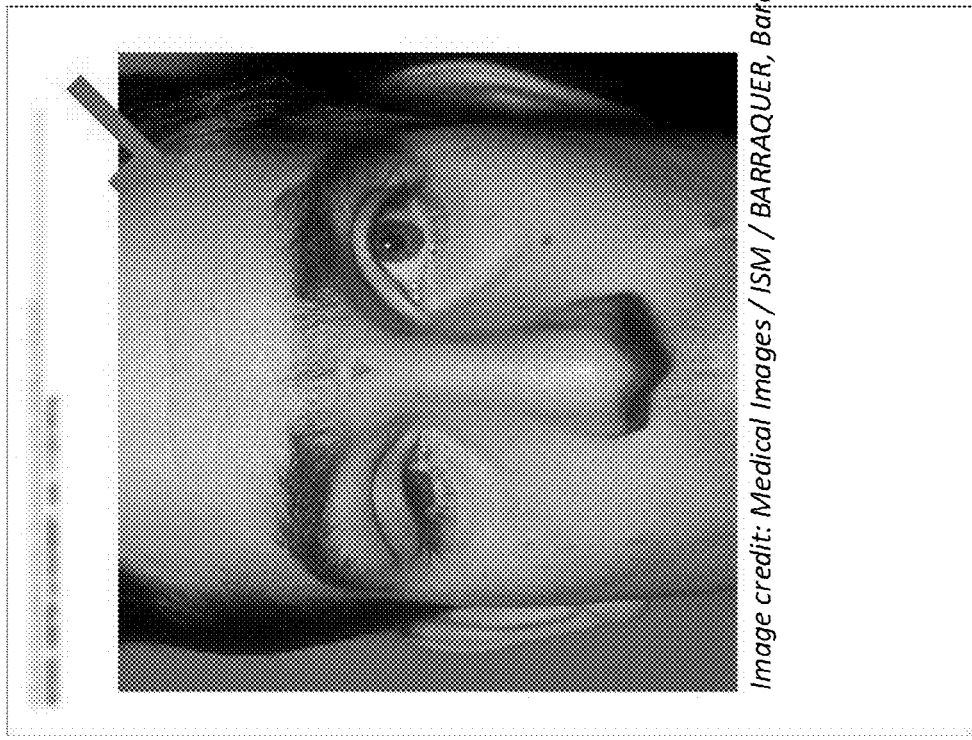
FIGS. 5A-14B illustrate example pre-processing related results of certain embodiments.
Figure 5A:
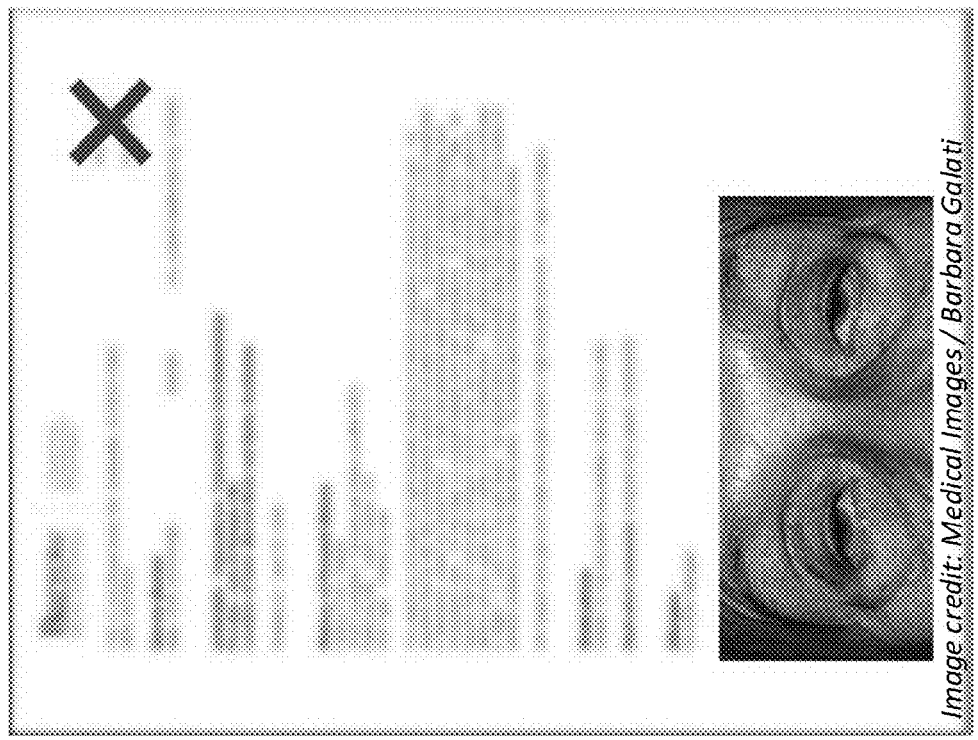

FIGS. 5A-5B illustrate differences between an image data file having an embedded image unsuitable for further analysis (FIG. 5A) and an image data file having an embedded image suitable for further analysis (FIG. 5B). Because the image data file of FIG. 5A has a high percentage of white pixels and a relatively small color photograph, the histogram color analysis determines that the number of white pixels exceeds a threshold value indicating the image data file is unsuitable for further analysis. By contrast, the image data file of FIG. 5B does not have a high percentage of white pixels or black pixels, as determined by a histogram color analysis, indicating that the image data file includes a color photograph of sufficient size for further analysis.

In certain embodiments, the image analysis system 65 may extract the embedded images of each image data file and discard the non-image portions of the image (e.g., through image boundary detection and cropping, or other relevant processes). In other embodiments however, further analysis is completed on those image data files identified as containing embedded images, without explicit image extraction processes.

d. Image Feature Detection

In many instances, original data files (e.g., reports) may comprise a plurality of embedded images, and thus the image analysis system 65 is configured to select a best image of the plurality of images for performing further analysis. The identification of a best image may be based at least in part on objective image analysis criteria relevant to later analysis of the content of the image, and thus, as indicated at Block 404 of FIG. 4, the image analysis system 65 may receive data identifying objective image analysis criteria. The objective image analysis criteria may comprise data identifying image features that should be shown within the image to facilitate further analysis, a desired orientation of the features for further analysis, and/or the like. As illustrated at Block 405, the image analysis system 65 utilizes deep-learning based image analysis to determine whether individual images contain image features that should be shown within the image and/or whether the individual images have an appropriate orientation (e.g., based on orientation of one or more features identified within the images).

As examples, the image analysis system 65 may receive objective image analysis criteria indicating that images are to be reviewed for patient facial features (e.g., specifically identifying eye-lid location for Blepharoptosis diagnosis), and thus the image analysis criteria may indicate that relevant images are photographs of a patient's face, taken normal to the patient's face, with the patient's eye lids open, and the patient looking at the camera. The image analysis system 65 may thus utilize a machine-learning based analysis to identify patient faces (distinguishing photographs of a patient's face from illustrations, company logos, and/or the like). Those images including a photograph of a patient's face may be identified regardless of orientation, and the image analysis system 65 may be configured to rotate images if necessary to standardize the orientation of the image for further analysis.

Figure 6A:
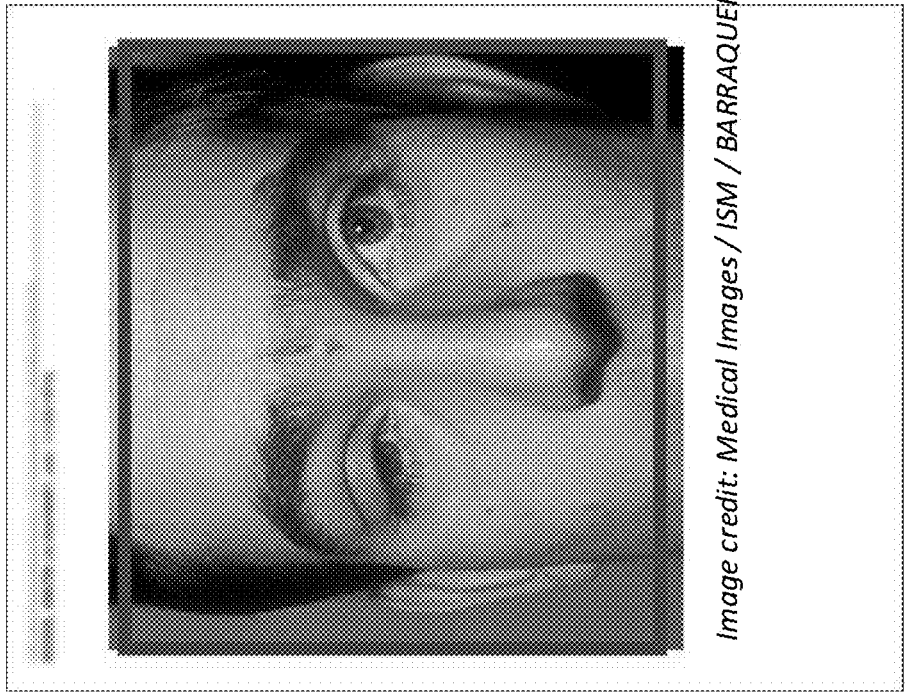
Figure 6C:
Figure 6B:
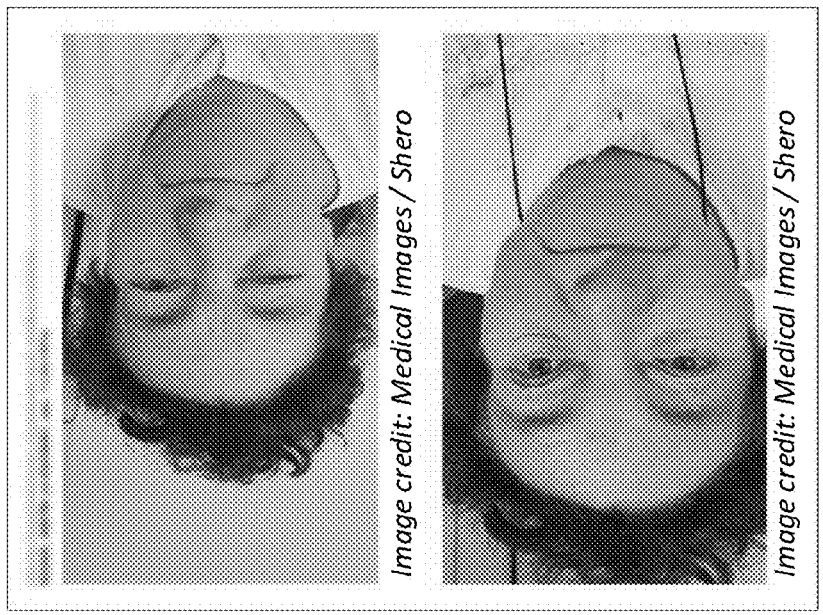

FIGS. 6A-6C illustrate the results of facial detection algorithms according to certain embodiments. For example, FIG. 6A illustrates a photograph of a face recognized by the image analysis system 65 and overlaid with a bounding box surrounding the detected face. As shown in FIGS. 6B-6C, the image analysis system 65 may be configured to identify facial features within rotated facial images (e.g., as shown in FIG. 6B), and to rotate those images to a desired orientation (as reflected by the rotation of the images from FIG. 6B to FIG. 6C) prior to providing a bounding box surrounding the detected face in each embedded image. It should be understood that other formatting processes beyond simply rotation of the images may be performed automatically in certain embodiments, such as resizing an image, sharpening an image, brightening an image, and/or the like.

As other examples, for image analysis relating to diagnoses of scoliosis, the image analysis system 65 may receive image analysis criteria indicating that images should be an X-ray image of a patient's spine with an orientation deemed clinically suitable for illustrating the presence or absence of scoliosis. In such instances, the image analysis system 65 is configured to utilize appropriate deep-learning based models to determine whether the included images are of the appropriate subject matter to support a diagnosis of scoliosis.

Figure 10:
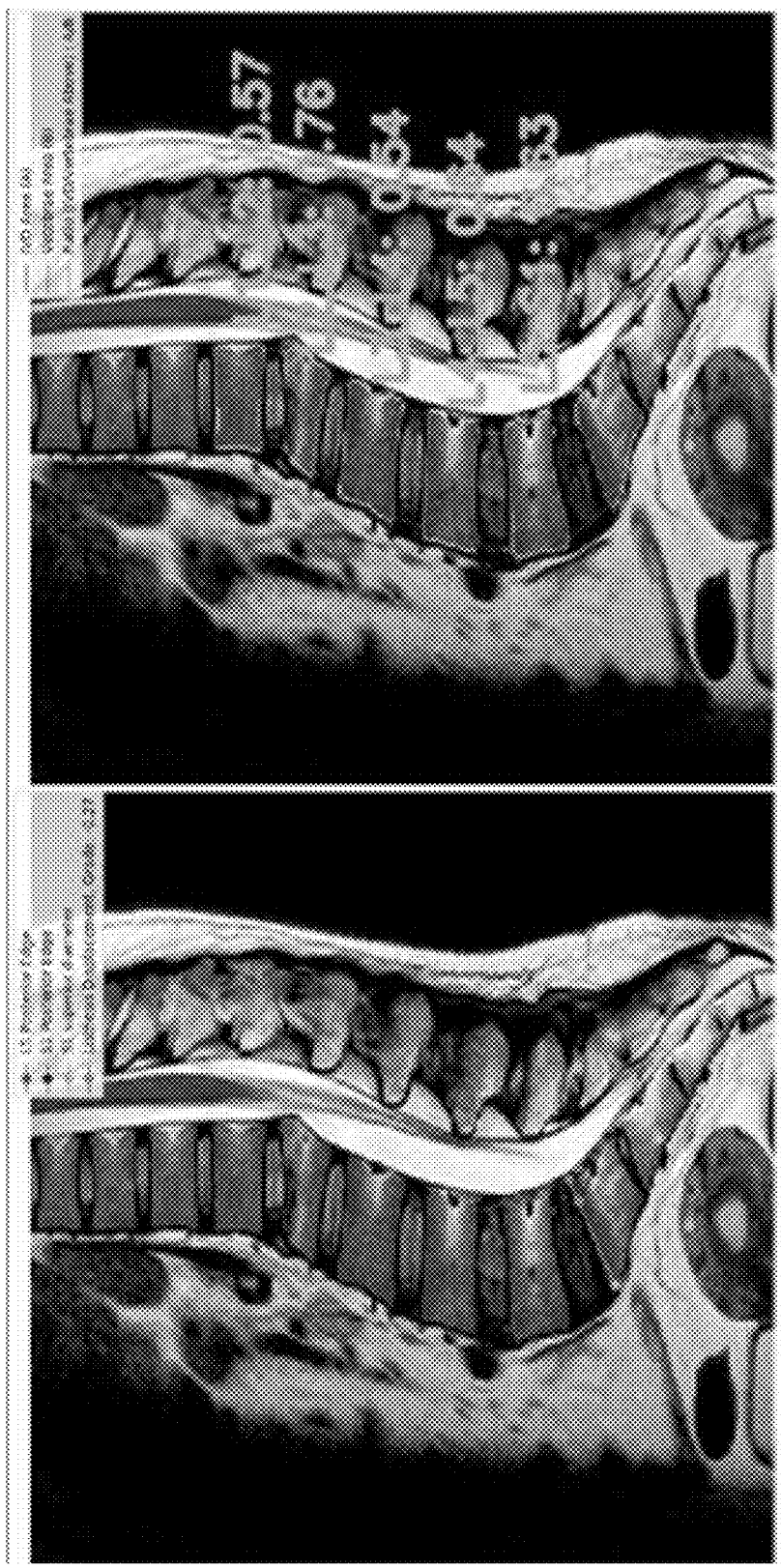

FIG. 10 provides yet another example of image types that may be provided for image analysis by the image analysis system 65, as well as certain example image-based analyses that may be performed with those images. As shown therein, the image analysis system 65 may receive image analysis criteria relating to image analyses for spine-based analysis, such as measuring lumbar vertebrae thinning, measuring spinal disk thicknesses, measuring spinal canal thicknesses, and/or the like. The image analysis criteria may specify that an X-Ray image should have a sagittal orientation, capturing at least a specified number of vertebrae for analysis. In certain embodiments, the image analysis criteria may specify that an entire length of a spinal canal should be visible within the image. The image analysis system 65 may utilize one or more models (e.g., classification models) to identify relevant features within a provided image to determine whether the image analysis criteria are satisfied (e.g., by identifying shapes of a top end and a bottom end of a spinal canal; by identifying shapes of one or more vertebrae, from a desired imaging orientation; and/or the like).

Figures 11A, 11B:
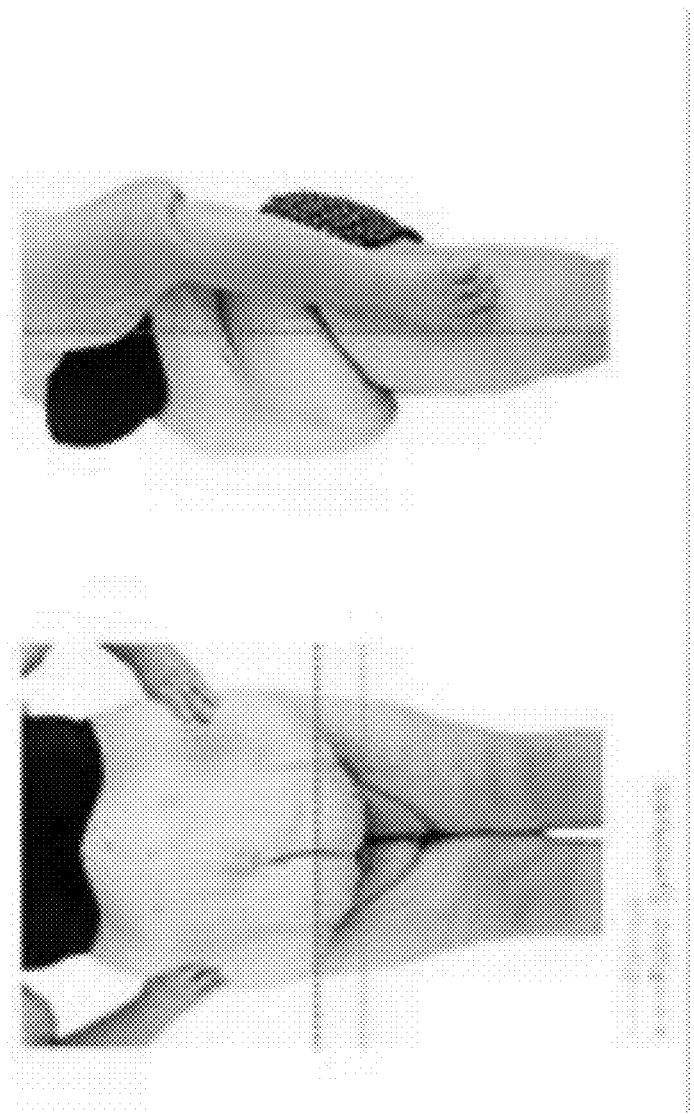

FIGS. 11A-11B provide yet another example of image types that may be provided for image analysis, for example, for measuring an abdominal panniculus relative to a pubic symphysis. As shown in the example of FIGS. 11A-11B, the image analysis system 65 may receive image analysis criteria requesting a frontal image of a patient's torso, showing an entirety of the patient's hip width. Consistent with the example shown, the image analysis criteria may specify that the image include an uninterrupted view of the patient's torso between the patient's neck/shoulders and the patient's knees. Moreover, the image analysis criteria may further specify a requirement for a side-view of the patient, showing the entirety of the patient's torso (e.g., between the patient's neck/shoulders and thighs or knees). The image analysis system 65 may implement a machine-learning based classification model to determine whether one or more submitted images satisfy applicable image analysis criteria for a particular image analysis process to be performed for the images.

Figure 12:
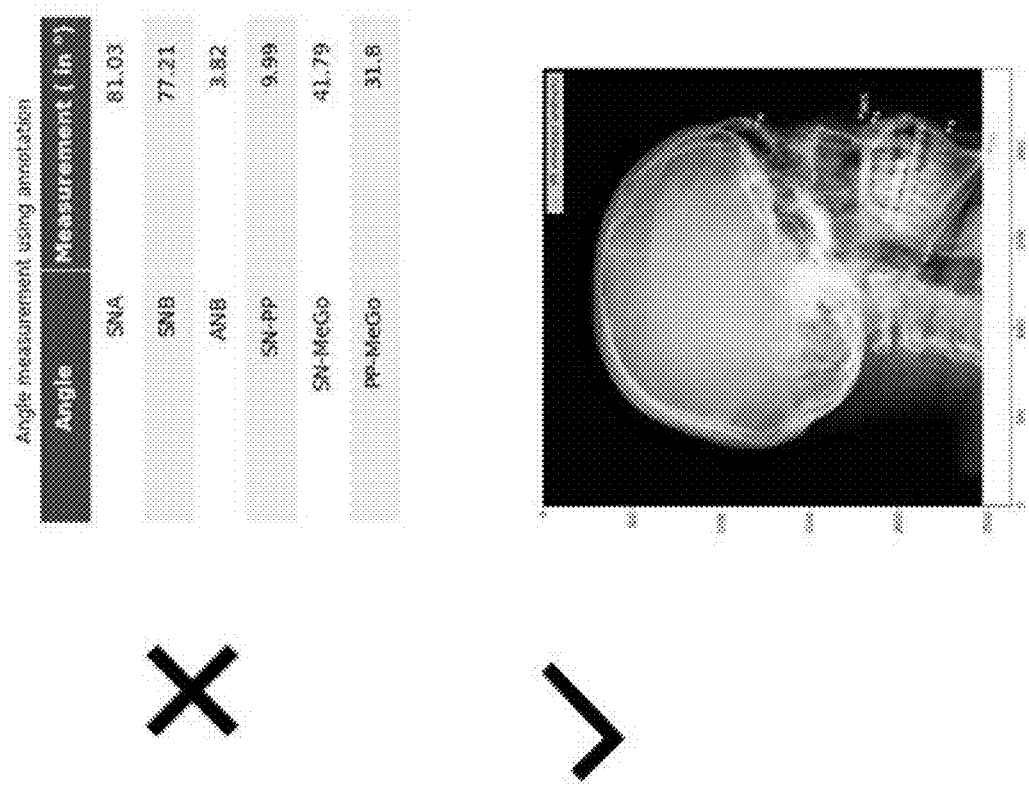

FIG. 12 provides yet additional examples of images that may be provided for image analysis, for example, for identifying lateral cephalometric x-ray images of sufficient quality to be utilized within later image analysis. As discussed herein with reference to blepharoptosis analyses, the image analysis criteria may specify one or more features to be identified within an image (e.g., those features to be utilized as landmarks for later image-based analysis). Accordingly, utilizing a machine-learning based classification model, the image analysis system may be configured to identify specific features within images presented to the image analysis system 65 to determine whether each of the required features specified within relevant image analysis criteria are identifiable within the image. With reference to the images shown in FIG. 12, certain images may be identified by the image analysis system 65 as failing to satisfy appropriate image analysis criteria, and such images may be excluded from further analysis (e.g., and a notification may be provided to the user computing entity that provided these images that the images are unusable for further analysis). For example, the images may be of insufficient resolution, may be of an incorrect orientation (e.g., as determined based on measurements between identified features within the image, example measurements being shown in the upper chart of FIG. 12), and/or may be of insufficient contrast for further analysis. By contrast, the image shown in the bottom of FIG. 12 may be provided in an appropriate orientation, with appropriate resolution that all features are identifiable, and with an appropriate resolution to identify relevant boundaries of the identifiable features.

Figure 13A:
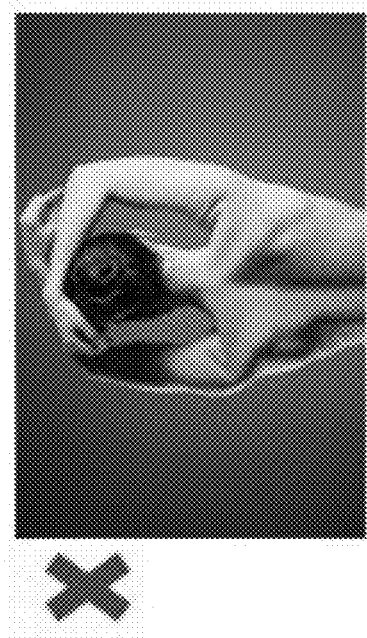
Figure 13B:
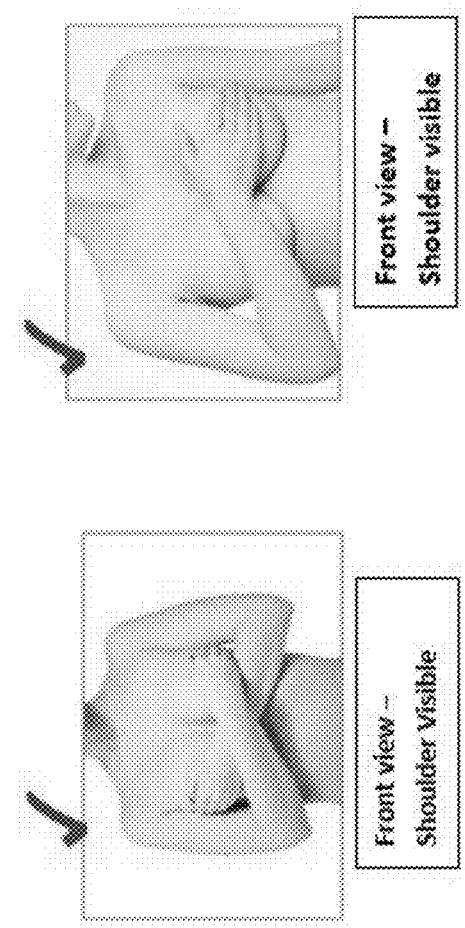

FIGS. 13A-13B provide yet another example of images that may be provided for image analysis, as well as an illustration of image analysis criteria that may be utilized for identifying images of sufficient content to enable detailed analysis thereof. For example, the image analysis criteria reflected within the images of FIGS. 13A-13B may be provided for an image-based analysis for determining whether a woman's breasts satisfy clinical criteria for breast reduction surgery. Although not shown, it should be understood that embodiments may be configured to identify and locate nipples within the image as features that may be used to ensure the images are of the proper content for further analysis.

The image of FIG. 13A is provided as an example image that does not satisfy applicable image analysis criteria. For example, images of an incorrect image content (e.g., images of a patient's back) may be excluded from analysis. Other criteria may specify that images of a text-only document and/or images of low-resolution images may be identified as failing to satisfy applicable image analysis criteria. As discussed above, non-color (e.g., black-and-white or greyscale) images may be excluded, as well as images containing multiple views within a single image. Moreover, the image analysis criteria may indicate that side-views, lateral views, oblique views, and cropped views (that do not show an entire necessary field of interest) may be excluded. As another example, the image analysis criteria may specify that certain features must be unobstructed within the image to be utilized as landmarks for further image analysis. As an example, the required landmarks may indicate that a patient's shoulders should be visible and unobstructed, and accordingly images with a patient's hair at least partially covering the patient's shoulders may be excluded from further analysis.

As shown in the example images of FIG. 13B, a frontal view of the patient, showing the entirety of the patient's shoulders may be identified as satisfying all applicable image analysis criteria for further image analysis. The image analysis system 65 may be configured to utilize a machine-learning based classification model trained to recognize specific features within an image to identify those images satisfying applicable image analysis criteria.

Figure 14A:
Figure 14B:
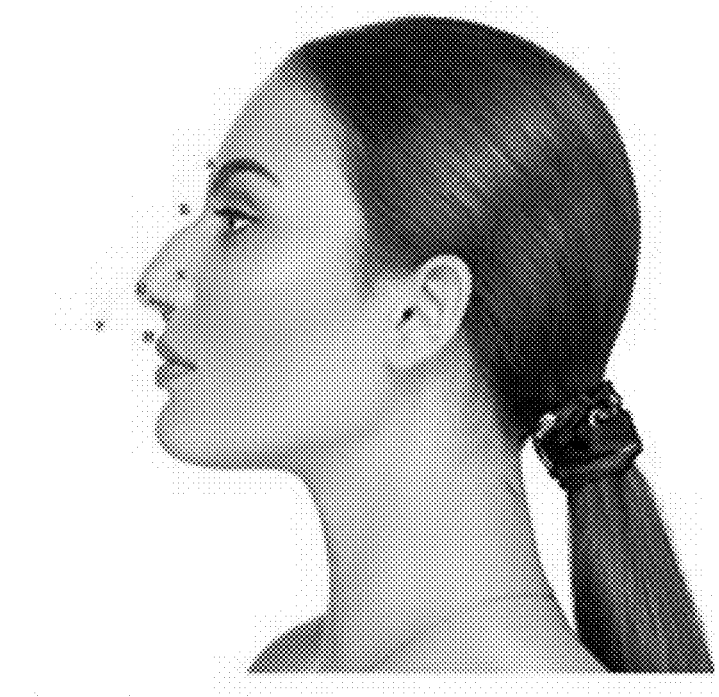

FIGS. 14A-14B illustrate yet other example images that may be provided to an image analysis system 65, for example, for automatically identifying whether a particular patient satisfies clinical criteria for a rhinoplasty based on a frontal view of the patient's nose or a side view of the patient's nose. As reflected by the image shown in FIG. 14A, the image analysis criteria may specify that a frontal-based analysis of a patient may require a frontal view of the patient's face. Certain embodiments may require specific features to be unobstructed in the image, such as a patient's iris, nose, and mouth. However the patient's face need not be entirely free of obstructions (e.g., with glasses, hair, and/or jewelry). FIG. 14B illustrates an example side-view that may satisfy applicable image analysis criteria for a side-view based rhinoplasty analysis. As shown, the image analysis system 65 may be configured to ensure the image is a side-orientation view showing the entirety of the patient's face, thereby enabling an identification of the location and shape of the patient's nose.

Generally, the image analysis system 65 is configured to receive relevant image analysis criteria based at least in part on a type of analysis to be performed later, and to receive a corresponding machine-learning model utilized to identify images that sufficiently illustrate relevant subject matter to enable later content-based image analysis. As just one example, a convolutional neural network (CNN) may be utilized to identify images satisfying appropriate criteria to ensure that those images illustrate content necessary for further image analysis, as indicated at Block 406 of FIG. 4. Moreover, upon identifying images containing appropriate content for further analysis, the image analysis system 65 may be configured to apply one or more additional filters, such as size-based filters to eliminate images that are not of sufficient size and/or quality for further content-based analysis. As just one example, the image analysis system 65 is configured to identify the size of each embedded image and to determine whether the size of each image satisfies a minimum size (e.g., 400 pixel by 400 pixel). Those images that have a size less than the minimum size may be excluded from further analysis (e.g., by discarding those image data files containing the embedded images and/or by assigning an appropriate metadata tag to the image data files to exclude those image data files from further analysis).

Moreover, the image analysis system 65 may be further configured to execute image signature matching processes to identify duplicate images, such that image analysis proceeds on a single image of a set of duplicate images. For example, a python-based image match process may be utilized to determine whether image signatures are sufficiently similar (e.g., by determining whether a generated image match score exceeds a defined threshold) to indicate that images are duplicates. It should be understood that other processes for identifying duplicate images may be utilized in other embodiments.

g. Image Quality Review

Upon identifying a subset of image data files containing images of sufficient quality for further review (the subset of image data files referred to herein as "analysis-ready image data files"), the image analysis system is configured to perform additional quality checks to ensure the images are of sufficient quality to support further substantive review of the contents of the images (as indicated at Block 407 of FIG. 4). Each of these quality checks may be performed in accordance with corresponding models, rule-based engines, and/or the like. Moreover, these quality checks may be performed in parallel or in series.

Figure 7A:
Figure 7B:
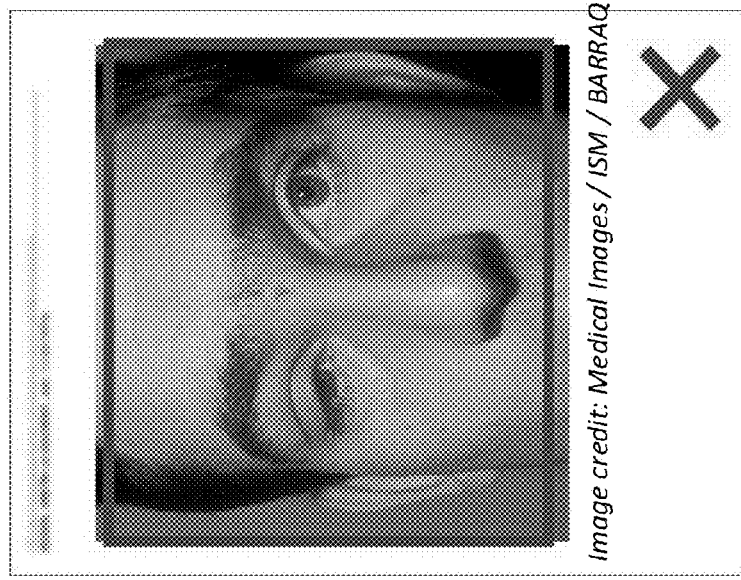

As just one example, reflected within the illustrations of FIG. 7A-7B, the image analysis system 65 may be configured to ensure displayed images are color photographs (e.g., full-color photographs), and not grayscale images. For example, a color-image analysis module may review RGB color values for each pixel within an embedded image to determine whether the image is a grayscale image or a color image. Grayscale images may be identified as comprising pixels having the same color value within each of the RGB color channels. The color-image analysis module may utilize a tolerance (e.g., +/−5 color values within each channel) to identify those images that are identified as grayscale images. Images determined to be grayscale images may be excluded from further analysis (e.g., by discarding the images or assigning a metadata flag to the containing image data file causing exclusion of the image data file from further analysis).

Figure 8B:
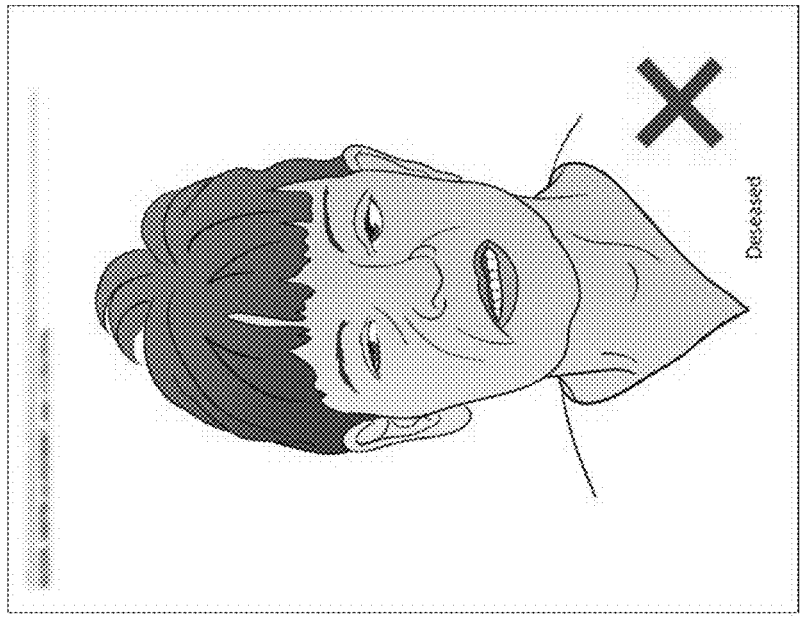
Figure 8A:
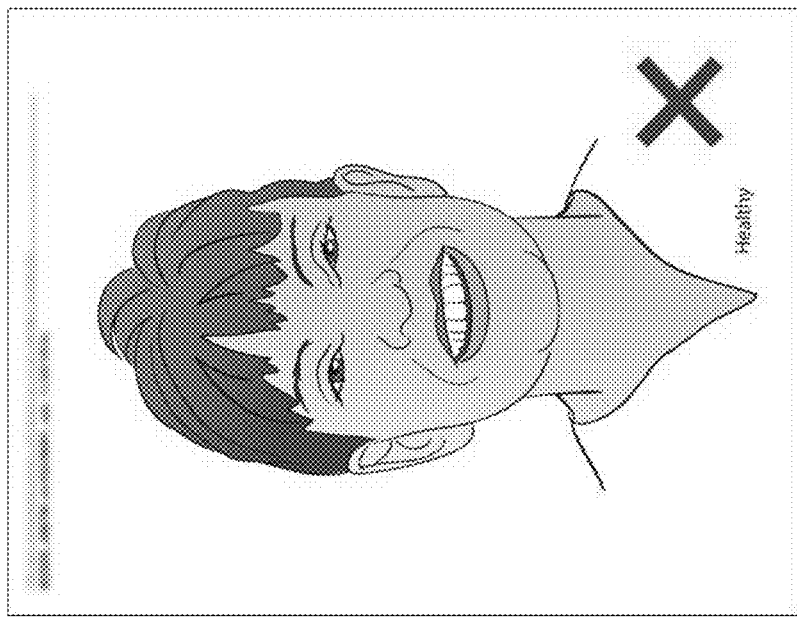

As another example, the image analysis system 65 may be configured to ensure images are photographs (or other appropriate imaging-device-generated images), rather than sketches (computer-generated or hand-drawn), if appropriate. The sketch-detection module may utilize a deep learning model trained utilizing a data set containing photographs and sketches, such as a convolutional neural network, to distinguish between sketches and photographs in certain embodiments (FIGS. 8A-8B are examples of sketches that may be excluded from analysis according to certain embodiments). Those images indicated as sketches may be excluded from further analysis (e.g., by discarding the images or assigning a metadata flag to the containing image data file causing exclusion of the image data file from further analysis). However, it should be understood that in certain instances, sketches may be desired for further analysis (e.g., for analyzing the steadiness of a patient's hand-drawing capability), and so such models may be excluded from a quality check, or such models may be utilized to exclude photographs, if relevant, according to certain implementations.

Figure 9B:
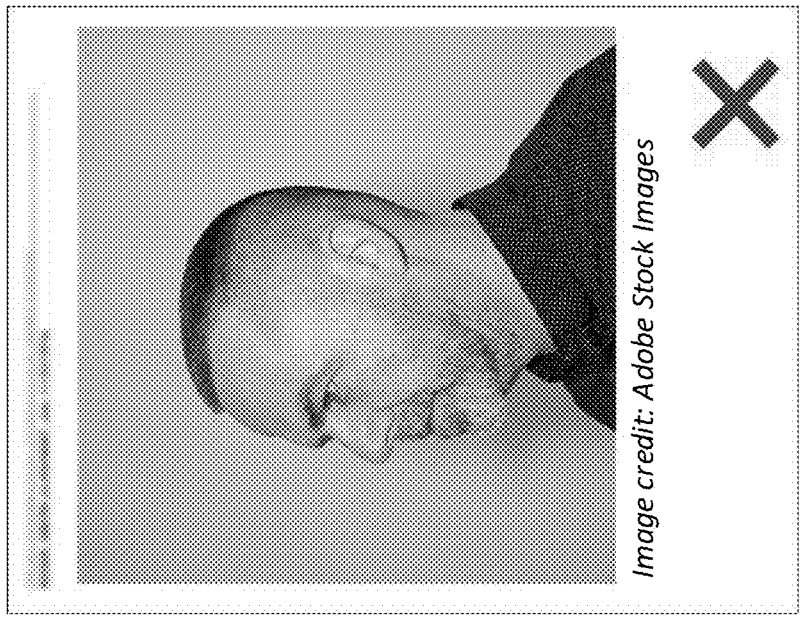
Figure 9A:
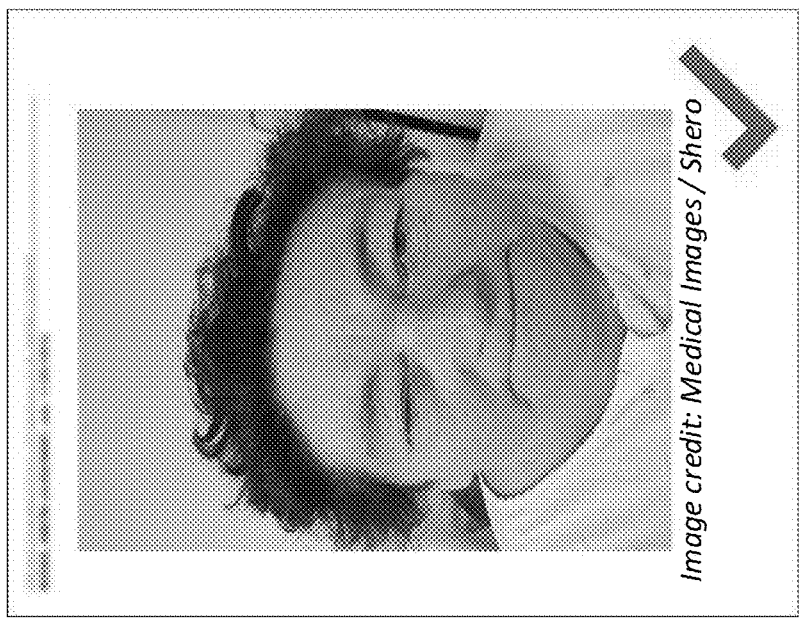

As other examples of quality checks according to certain embodiments, the image analysis system may be configured for performing content-based analyses, based at least in part on the previously-discussed objective image analysis criteria. These content-based quality checks may utilize deep-learning based analysis to ensure the content of the images are as needed for further analysis. As a specific example, a content-based quality check may identify the orientation of specific features, such as the orientation of a face within an image, as reflected within FIGS. 9A-9B. As a specific example, detailed content analysis may require a frontal-image of a face (as illustrated in FIG. 9A), such that images taken from a different orientation (such as the side-angle orientation of FIG. 9B) may be identified as insufficient for further analysis. Other image criteria may identify whether the images comprise necessary content and/or whether features identified within images have a desired orientation relative to other features within the image (e.g., identifying the location of eyelids to ensure a patient's eyes are open within the photo). Other examples are discussed above, such as identifying an orientation of a spinal x-ray, an orientation of a patient's body within an image, an orientation of a patient's face within an image, and/or the like. Additional content-based analyses may be performed in accordance with the requirements of a specific image analysis, such as those discussed herein.

h. Image Prioritization

In addition to the above-described concepts for removing duplicate images from further analysis, the image analysis system 65 of certain embodiments is configured to prioritize images in instances in which a plurality of images are deemed suitable for further analysis (e.g., by satisfying appropriate criteria as discussed above). The prioritization process may proceed via a machine-learning based model, such as a convolutional neural network configured for reviewing each image deemed suitable for further analysis relative to a training data set. The training data set may be utilized with a supervised machine-learning model to indicate images within the training data set deemed appropriate or best for further analysis. Utilizing this training data set, the image analysis system 65 may assign a match score to each image deemed suitable for further analysis within the image data set, such that the match score is indicative of the level of match between the embedded image and the training data set. The match scores for all of the images deemed suitable for further analysis may be compared to generate a prioritization ranking of the images and a highest match score may be indicated as providing a best image of the plurality of images deemed suitable for further analysis. While all of the images deemed suitable for further analysis may be provided to appropriate down-stream analytical modules, those images may be provided in order of priority, or the down-stream analytical module may be configured to begin analysis with the best-ranked image, and may only proceed to analyze further images upon determining that the best-ranked image is deemed unsuitable for establishing a conclusion with respect to an analysis to be performed.

In certain embodiments, the image analysis system 65 may determine that no embedded images within the documentation (e.g., PDF files, image files, and/or the like) submitted satisfy applicable criteria for further analysis. In such instances, the image analysis system 65 may be configured to generate a notification to be provided to a user computing entity 30 providing the original data files indicating that additional images are necessary to complete further automated analysis. To facilitate the submission of quality images without undue burden on users (e.g., care providers, patients, and/or the like), the foregoing pre-processing of images may occur in real-time or near real-time, such that the image analysis system 65 may be configured to provide feedback to the user shortly after submission of the original documents (and preferably during a single interactive session between the user computing entity 30 and the image analysis system 65).

In certain embodiments, the image analysis system 65 may be accessible to user computing entities 30 via an interactive, web-based tool that may be accessed via a browser application executing on the user computing entity 30. Through the web-based tool, a user may upload one or more original documents for image analysis, causing the user computing entity 30 to transmit the original document to the image analysis system 65 for pre-processing (and ultimately for substantive review in certain embodiments). As another example, the user computing entity 30 may be configured to execute or access a document management system (e.g., storing documents locally on the user computing entity 30 or storing documents within a cloud-based storage location), and the web-based tool may enable a user computing entity 30 to initiate a transfer of documents from the document management system to the image analysis system 65. Upon receipt of original documents at the image analysis system 65, the image analysis system 65 may initiate the image extraction and pre-processing methodology as discussed herein, such that the image analysis system 65 may be configured to provide a responsive indication of whether the submitted original documents include embedded images that satisfy applicable criteria enabling automated analysis thereof. Moreover, it should be understood that the user computing entity 30 may be configured to provide images to the image analysis system 65 via any of a variety of mechanisms. For example, the user computing entity 30 may be configured to utilize an included camera (e.g., a still camera, a video camera, a webcam, and/or the like) providing image data to an application executing on the user computing entity 30 that is configured to provide image data to the image analysis system 65. In those instances in which video data is provided, the video data comprises a plurality of images (e.g., arranged in a chronological sequence) that may be individually analyzed (e.g., via machine-learning based models) to identify relevant images for further analysis, for example, as containing representations of features indicated as relevant for further analysis.

Although discussed in reference to an automated real-time or near real-time analysis of original documents, it should be understood that the image analysis system 65 of certain embodiments maybe configured for pre-processing original documents in accordance with alternative timing of processing, such as batch-based processing, periodic processing, and/or the like.

Moreover, as noted herein, the image analysis system 65 may be configured to transmit the extracted images to one or more downstream image analysis modules (and/or the image analysis system 65 may be additionally configured to execute one or more image analysis modules for performing substantive analysis of the images. Such additional analysis may be performed in accordance with the configurations discussed in co-pending U.S. patent application Ser. No.

17/191,921, filed concurrently with the present application, the contents of which are incorporated herein by reference in their entirety.

IV. CONCLUSION

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A computer-implemented method comprising:
   receiving, using one or more processors, a source data file containing one or more images;
   standardizing, using the one or more processors, the source data file to a defined file type to generate a standardized source data file;
   performing, using the one or more processors, histography color segmentation to identify images within the standardized source data file;
   extracting, using the one or more processors, one or more of the identified images from the standardized source data file;
   executing, using the one or more processors, a machine-learning based model for identifying features within the one or more extracted identified images; and
   aligning, using the one or more processors, the extracted images based at least in part on the identified features.

2. The computer-implemented method of claim 1, further comprising:
   filtering, using the one or more processors and a machine-learning based filtering model, the one or more extracted identified images having a defined image type.

3. The computer-implemented method of claim 2, wherein filtering the one or more extracted identified images comprises selecting full-color images.

4. The computer-implemented method claim 2, wherein filtering the one or more extracted identified images comprises distinguishing between one or more photographs and one or more illustrations, and selecting the one or more photographs.

5. The computer-implemented method of claim 1, wherein aligning the one or more extracted identified images comprises rotating the one or more extracted identified images based at least in part on the identified features.

6. The computer-implemented method of claim 1, further comprising:
   receiving, using the one or more processors, objective image analysis criteria,
   wherein executing, using the one or more processors, the machine-learning based model causes identification of one or more finalized images of the one or more extracted identified images satisfying the objective image analysis criteria.

7. The computer-implemented method of claim 6, wherein the objective image analysis criteria defines an image content orientation.

8. A system comprising:
   one or more non-transitory memory storage areas; and
   one or more processors collectively configured to:
      receive a source data file containing one or more images;
      standardize the source data file to a defined file type to generate a standardized source data file;
      perform histography color segmentation to identify images within the standardized source data file;
      extract one or more of the identified images from the standardized source data file;
      execute a machine-learning based model for identifying features within the one or more extracted identified images; and
      align the one or more extracted identified images based at least in part on the identified features.

9. The system of claim 8, wherein the one or more processors are further configured to:
   filter, using a machine-learning based filtering model, the one or more extracted identified images having a defined image type.

10. The system of claim 9, wherein to filter the one or more extracted identified images, the one or more processors are further configured to select one or more full-color images.

11. The system of claim 9, wherein to filter the one or more extracted identified images, the one or more processors are further configured to distinguish between one or more photographs and one or more illustrations, and to select the one or more photographs.

12. The system of claim 8, wherein to align the one or more extracted identified images the one or more processors are further configured to rotate the one or more extracted identified images based at least in part on the identified features.

13. The system of claim 8, wherein the one or more processors are further configured to:
   receive objective image analysis criteria,
   wherein to execute the machine-learning based model causes identification of one or more finalized images of the one or more extracted identified images satisfying the objective image analysis criteria.

14. The system of claim 13, wherein the objective image analysis criteria defines an image content orientation.

15. A computer program product comprising at least one non-transitory computer-readable storage medium having computer-readable program code portions stored therein, the computer-readable program code portions configured to:
   receive a source data file containing one or more images;
   standardize the source data file to a defined file type to generate a standardized source data file;
   perform histography color segmentation to identify images within the standardized source data file;
   extract one or more of the identified images from the standardized source data file;
   execute a machine-learning based model for identifying features within the one or more extracted identified images; and
   align the one or more extracted identified images based at least in part on the identified features.

16. The computer program product of claim 15, further comprising one or more executable portions configured to:
   filter, using a machine-learning based filtering model, the one or more extracted identified images.

17. The computer program product of claim 15, wherein to filter the one or more extracted identified images the one or more executable portions are further configured to select one or more full- color images.

18. The computer program product of claim 15, wherein to filter the one or more extracted identified images the one or more executable portions are further configured to distinguish one or more photographs and one or more illustrations, and to select the one or more photographs.

19. The computer program product of claim 15, wherein to align the one or more extracted identified images the one or more executable portions are further configured to rotate the one or more extracted identified images based at least in part on the identified features.

20. The computer program product of claim 15, further comprising one or more executable portions configured to:
   receive objective image analysis criteria,
      wherein executing the machine-learning based model causes identification of one or more finalized images of the one or more extracted identified images satisfying the objective image analysis criteria.

21. The computer program product of claim 20, wherein the objective image analysis criteria defines an image content orientation.

* * * * *

UNITED STATES PATENT AND TRADEMARK OFFICE
CERTIFICATE OF CORRECTION

PATENT NO. : 12,131,475 B2  
APPLICATION NO. : 17/191868  
DATED : October 29, 2024  
INVENTOR(S) : Russell H. Amundson et al.

It is certified that error appears in the above-identified patent and that said Letters Patent is hereby corrected as shown below:

In the Claims

In Column 21, Lines 34-35, Claim 1, delete "the extracted images" and insert -- the one or more extracted identified images --, therefor.

In Column 21, Line 45, Claim 4, delete "method claim" and insert -- method of claim --, therefor.

In Column 22, Line 67, Claim 17, delete "full- color" and insert -- full-color --, therefor.

Signed and Sealed this  
Fourteenth Day of January, 2025

Derrick Brent  
*Acting Director of the United States Patent and Trademark Office*